United States Patent [19]
Law et al.

[11] Patent Number: 5,914,271
[45] Date of Patent: Jun. 22, 1999

[54] FERTILITY TEST

[75] Inventors: Wai Tak Law, Moorestown; Robert Harper, Mount LAurel, both of N.J.

[73] Assignee: ActiMed Laboratories, Inc., Burlington, N.J.

[21] Appl. No.: 08/842,773

[22] Filed: Apr. 17, 1997

Related U.S. Application Data

[60] Provisional application No. 60/016,338, Apr. 19, 1996.

[51] Int. Cl.⁶ .............................. G01N 33/48; A61B 10/00
[52] U.S. Cl. ................................ 436/65; 436/73; 436/74; 436/79; 436/164; 436/166; 436/169; 600/551
[58] Field of Search .................................. 436/65, 73, 74, 436/79, 164, 166, 169; 600/551

[56] References Cited

U.S. PATENT DOCUMENTS

| | | |
|---|---|---|
| 2,824,842 | 2/1958 | Sulkowitch . |
| 3,006,735 | 10/1961 | Jordan . |
| 3,434,801 | 3/1969 | Scherr . |
| 3,457,045 | 7/1969 | Fraguada et al. . |
| 3,754,865 | 8/1973 | Gindler . |
| 3,798,000 | 3/1974 | Helger . |
| 3,813,222 | 5/1974 | La Vietes . |
| 3,854,880 | 12/1974 | Rathje . |
| 3,934,977 | 1/1976 | Cleaver . |
| 3,938,954 | 2/1976 | Stavropoulos et al. . |
| 4,010,738 | 3/1977 | Preti et al. . |
| 4,119,089 | 10/1978 | Preti et al. . |
| 4,151,831 | 5/1979 | Lester . |
| 4,293,307 | 10/1981 | Simpson et al. . |
| 4,358,288 | 11/1982 | Goldman . |
| 4,382,122 | 5/1983 | Mezei . |
| 4,383,043 | 5/1983 | Denney et al. . |
| 4,385,125 | 5/1983 | Preti et al. . |
| 4,399,003 | 8/1983 | Sarig et al. . |
| 4,425,427 | 1/1984 | Luderer . |
| 4,454,230 | 6/1984 | Denney . |
| 4,503,156 | 3/1985 | Yamazato et al. . |
| 4,532,217 | 7/1985 | Springer, Jr. et al. . |
| 4,594,225 | 6/1986 | Arai et al. . |
| 4,618,587 | 10/1986 | Premoli et al. . |
| 4,724,216 | 2/1988 | Young et al. . |

(List continued on next page.)

FOREIGN PATENT DOCUMENTS 8301735  5/1983  WIPO .

OTHER PUBLICATIONS

C. G Hartman *Fertil. Steril.* 1965, 16, 771–776.
J.G. Henrotte et al, Symp. Int. Deficit Magnesique Pathol. 1st, 1971, 91–109.
C. Dawes *International J. Chronobiol.* 1974, 2, 253–279.
I. D. Mandel et al. *Oral. Sci. Reviews* 1976, 25–47.
P. A. Sebestia et al. *Clin. Chim. Acta* 1976, 68, 309–311.
S. Mancuso et al, *Acta. Med. Rom.* 1978, 16, 387–403.
H. Ben–Aryeh et al. *Revue Francaise de Gynecolgie et d Obstetrique*, 1978, 73, 777–782.
F. Lagerloef *Clin. Chim. Acta.* 1980, 102, 127–135.
B. H. Albrecht et al, *Fertil. Steril.* 1985, 44, 200–205.
R. S. Fernando et al. *Fertil. Stevil.* 1987, 47, 409–415.
S. Valente *Clin. Exp. Obstet. Gynecol.* 1988, 15, 66–70.
A. K. Pandya et al. *Indian J. Physiol. Pharmacol.* 1995, 39, 411–414.
Bauman, Joan E., "Basal Body Temperature: Unreliable Method Ovulation Detection", Fertility and Sterility, v. 36, No. 6, pp. 729–733, 1981.

(List continued on next page.)

*Primary Examiner*—Arlen Soderquist
*Attorney, Agent, or Firm*—Iver P. Cooper

[57] ABSTRACT

The fertile period in a female can be detected by monitoring the calcium and magnesium concentrations in unstimulated saliva. In the three to five day period immediately prior to ovulation, the calcium and magnesium concentrations of saliva drop. This concentration monitoring can be done by any conventional means for quantitatively assaying calcium or magnesium, such as by flow through tests, test strips, cards, charts, probes, meters, and the like.

8 Claims, 3 Drawing Sheets

U.S. PATENT DOCUMENTS

| | | |
|---|---|---|
| 4,753,890 | 6/1988 | Smith-Lewis et al. . |
| 4,770,186 | 9/1988 | Regas et al. . |
| 4,795,712 | 1/1989 | Toner et al. . |
| 4,820,647 | 4/1989 | Gibbons . |
| 4,870,024 | 9/1989 | Musacchio et al. . |
| 4,871,678 | 10/1989 | Wahl et al. . |
| 4,871,679 | 10/1989 | Tanaka et al. . |
| 4,904,605 | 2/1990 | O'Brien et al. . |
| 4,966,784 | 10/1990 | Tanaka et al. . |
| 4,992,382 | 2/1991 | Porter et al. . |
| 5,055,407 | 10/1991 | Lau et al. . |
| 5,057,435 | 10/1991 | Denney . |
| 5,077,221 | 12/1991 | Miller, Jr. et al. . |
| 5,108,905 | 4/1992 | Sunahara et al. . |
| 5,192,691 | 3/1993 | Quinn et al. . |
| 5,215,922 | 6/1993 | Artiss et al. . |
| 5,215,925 | 6/1993 | Babb et al. . |
| 5,262,330 | 11/1993 | Chapoteau et al. . |
| 5,300,439 | 4/1994 | Charlton . |
| 5,310,888 | 5/1994 | Bloczynski et al. . |
| 5,350,694 | 9/1994 | Zimmerle . |
| 5,397,710 | 3/1995 | Steinman . |
| 5,409,835 | 4/1995 | Lakowicz et al. . |
| 5,424,214 | 6/1995 | Shu et al. . |
| 5,460,972 | 10/1995 | Altura et al. . |
| 5,482,866 | 1/1996 | Denton et al. . |
| 5,496,522 | 3/1996 | Vo-Dinh et al. . |
| 5,501,980 | 3/1996 | Katerinopoulos et al. . |

OTHER PUBLICATIONS

Frenkel, David A., "Sperm Migration and Survival in the Endometrial Cavity", Int. J. Fertil., vol. 6, pp. 285–290, 1961.

Liskin, "Periodic Abstinence: How Well Do New Approaches Work?", Population Reports, vol. 9, No. 4, pp. 33–71, 1981.

Puskulian, Louiza, "Salivary Electrolyte Changes During the Normal Menstrual Cycle", J. Dent. Res. (supplement to No. 5), vol. 51, pp. 1212–1216, 1972.

Tenovuo et al., "Evaluation of Salivary Markers during the Menstrual Cycle: Peroxidase, Protein, and Electrolytes", Biochemical Medicine, vol. 25, pp. 337–345, 1981.

Wilcox et al., "Timing of Sexual Intercourse in Relation to Ovulation", The New England Journal of Medicine, vol. 333, No. 23, pp. 1517–1521, 1995.

Fehring, R., "A Comparison of the Peak in Cervical Mucus with the Ovulon Fertility Monitor in Determining the Fertility Period", Conception Technology Inc.: Clinical Studies Abstract, Nov. 1995.

Rydberg, Erik, "Observations on the Crystallization of the Cervical Mucus", Acta Obstetricia et Gynecologica Scandinavica, vol. 28, pp. 172–187, 1948

FERTILITY TEST

This application claims priority, under §119 (e), from U.S. Provisional Application No. 60/016,338, filed Apr. 19, 1996.

FIELD OF THE INVENTION

The present invention relates to a method for predicting and detecting the fertile period of a female, including a human female.

BACKGROUND OF THE INVENTION

An important step in the evaluation and management of female fertility is the detection and timing of the actual fertile period. It is of great importance to determine the precise time of human fertility in order to enhance the chances of conception, either naturally or by artificial insemination.

Alternatively, if human birth control is desired, knowledge of the actual fertile period allows one to prevent conception with a minimum of adverse effects, i.e., limiting use of contraceptive drugs to the fertile period, or avoiding sexual intercourse only during that period.

For breeders of animals, it is important to know the fertile period of the female animal to ensure that fertilization occurs and that offspring are produced. This determination is useful to owners of pets, such as cats and dogs, as well as to breeders of livestock and particularly to breeders of thoroughbred race horses or cattle.

There is now believed to be only about a three to six day window each cycle during which a woman can conceive, which is the three to six days prior to ovulation, rather than the period immediately prior to and following ovulation. As reported by Wilcox et al. in NEJM 333(23): 1517–1521 (1995), a woman's fertile period lasts about six days and ends on the day of ovulation. Therefore, fertility tests based upon detection of ovulation detect a period too late to be useful in determining fertility of a female.

There has long been a need for a simple but reliable method for predicting and confirming the fertile period which can be conducted in the privacy of the home. Because of religious, philosophic, or health considerations, the preferred method of birth control for many is by periodic abstinence, also known as the "rhythm method." This method involves identifying the fertile period using an available method, or more often, simply by a guess based on the length of the menstrual cycle, and then avoiding coitus during this period. Ovulation is assumed to occur mid-cycle, and the period of abstinence is adjusted accordingly. This technique has proven highly unreliable at best, in part because of the previous belief that the fertile period coincided with a period shortly before and shortly after ovulation. Although it was believed that the unreliability of the rhythm method was largely due to the inability to accurately predict and confirm ovulation, it is now recognized that the problem partly arose from a misunderstanding of exactly when in a woman's cycle the fertile period actually occurs. For couples wishing to conceive, it is important to know the period during which the female is most fertile to increase the chances of a pregnancy occurring. Similarly, the success of therapeutic measures such as artificial insemination depends upon adequate documentation and timing of the fertile period.

The precise fertilizing life span of spermatozoa is not known. It has been reported that human sperm can survive within the female reproductive tract for up to seven days (Frenkel, *Int. J. Fertil* 6:285, 1961). However, on the basis of anecdotal information and indirect evidence, most reproductive biologists believe that the human spermatozoon loses its ability to fertilize the ovum within two or three days.

Additionally, accurate information on the longevity of the human ovum is not available. Data from primate studies and pregnancies resulting after timed coitus or insemination indicate that the capacity of the human ovum to be fertilized does not extend beyond 24 hours after follicular rupture.

With the lack of information about these variables, the best estimate is that a period of abstinence (or contraception) of three to five days before and two days after the fertile period is essential for avoiding conception. Unfortunately, no precise, simple, and practical method for detecting the fertile period in a female has hitherto been available.

One method for detecting fertility, known as the sympto-thermal method, involved a subjective evaluation of basal body temperature and cervical mucus to determine the time of ovulation, and, it was hoped, the fertile period. This method requires intensive user training in the method and relatively high failure rates were and are still unavoidable.

In another procedure, changes in cervical mucus were combined with basal body temperature to identify the onset and end of the fertile period based upon approximate time of ovulation. There are several disadvantages with this approach, some of them being the need for immobility before taking the temperature, daily monitoring the cervix and vagina, and subjective interpretation of vaginal mucus quality and of the BBT trend. The technique is difficult to learn, with one to six months of careful training and supervision being required to acquire proficiency.

Another method for determining the fertile period based on estimating time of ovulation, is by basal body temperature charting. The only equipment necessary for basal body temperature monitoring is a basal body thermometer, which is inexpensive. However, most of these tests provide evidence of ovulation only after it has occurred, which is too late to provide an indication of the entire fertile period. Another relatively serious problem is the variation of the relation between the basal body temperature and the peak mucus symptoms. In one study, in 25 of the cases, the temperature rise occurred more than two days before or two days after the peak symptom, Liskin, *Population Reports,* 9, No. 4, pp. 33–65, 1981. Furthermore, basal body temperature reflects ovulation in only about 70% of cycles, since monophasic (non-indicative) basal body temperature curves are frequently seen in ovulatory cycles, Bauman, *Fertility and Sterility,* 36, pp. 729–733. When used for birth control, failure rates of up to 34% have been recorded with this method.

Although computerized interpretation of data is now available for the sympto-thermal method, as disclosed in U.S. Pat. No. 4,151,831 and in WO 83/01735, the disadvantages inherent in the physiological parameters used in the method are still limiting factors.

Secretion of cervical mucus is regulated by ovarian hormones. Estrogen stimulates the production of large amounts of thin, watery, alkaline, acellular cervical mucus with intense ferning, spinnbarkeit and sperm receptivity. Progesterone inhibits the secretory activity of cervical epithelia and produces scanty, viscous, cellular mucus with low spinnbarkeit and absence of ferning, which is impenetrable by spermatozoa. Changes in the appearance of the cervix and physical properties and chemical constituents of cervical mucus form the basis for many tests commonly used to determine the time of ovulation. These include the appearance of the cervix, midcycle mucorrhea, crystallization of the cervical mucus, spinnbarkeit, viscosity or consistency of the cervical mucus, and cyclic changes of various constituents of the cervical mucus. Unfortunately, these tests require skill and experience to be employed efficiently.

Hormonal blood testing gives better prediction of the exact ovulation time, but this requires expensive instrumentation to collect the quantitative measurements. The identification of a preovulatory rise in estrogens followed by a peak in luteinizing hormone (LH) concentration as determined by radioimmunoassay is a good indication of imminent ovulation, but this method is also expensive and cannot be done at home. Frequently, several samples of blood, drawn at mid-cycle, will be analyzed for luteinizing hormone concentrations. These techniques are expensive and require several visits to a hospital or medical laboratory having the appropriate analytical facilities. Unfortunately, the mean interval between the LH peak and the estimated time of ovulation has been shown to be less than 48 hours in all cycles, and less than 24 hours in 75% of cycles. This may not be a sufficient window for determining the most fertile period, which is now believed to be 3–6 days prior to ovulation.

Serum estradiol demonstrates a characteristic peak approximately one day before the LH surge and 37 hours prior to ovulation. Thus, serial determinations of serum estradiol at midcycle can detect the time of ovulation with a fair amount of accuracy. Serum progesterone levels are usually less than 1 ng/ml during the follicular phase. Coincidentally with the LH surge, the serum progesterone concentration begins to rise and reaches a peak of greater than 10 ng/ml approximately eight days after the LH peak. Most investigators consider a progesterone level greater than 5 ng/ml predicts ovulation. Presumption of ovulation can be documented, then, by obtaining two blood samples, on days 8 and 21 of a normal cycle. An increase of the progesterone value from less than 1 ng/ml to greater than 5 ng/ml would be consistent with ovulation.

Assay of pregnane diol, a metabolite of progesterone, from urine, also would aid in ovulation detection. In the midluteal phase, pregnanediol levels reach 4 to 6 mg/24 hours. A unitary level of 2 mg or greater is thus consistent with ovulatory cycles. The process of ovulation can also be monitored and detected using ultrasonography. Daily visits to a center equipped with the sophisticated instrumentation used for the procedures are necessary. Several means are required by mid-cycle to pinpoint ovulation by observing follicular development and subsequent ovum release. While accurate identification of ovulation is possible with this technique, it is of little value as a self-monitoring method for purposes of enhancing or reducing fertility.

Several methods of predicting ovulation based on biochemical changes in various body fluids such as vaginal secretions, saliva, or urine have been proposed. The major drawback of these methods is that there is a significant variation in the component being measured between individuals, so that it is difficult to set ranges which are meaningful for a large population. In one method, where the lactic acid concentration of vaginal secretions was proposed as an indicator of impending ovulation, the variability of its concentration between individuals as great as one thousand percent, cf. U.S. Pat. No. 4,010,738.

In-home ovulation prediction tests such as the monoclonal antibody based urine tests (Clearplan Easy, First Response, Q test) detect increasing concentration of luteinizing hormone (LH) in the urine. The LH surge precedes ovulation by approximately 20–48 hours and can usually be detected in the urine 8–12 hours after it occurs in the serum. Therefore, one can predict ovulation 1–2 days before it happens using these tests. Unfortunately, predicting ovulation one to two days in advance is not sufficient to detect the entire fertile period of a female; a three to six day prediction is required.

Preti et al, in U.S. Pat. No. 4,385,125, disclose that ovulation can be detected by monitoring concentrations of dodecanol in saliva. However, this assay is limited to detecting ovulation, not a fertile period, as the spike in dodecanol concentration precisely corresponds to ovulation.

Preti et al. in U.S. Pat. No. 4,010,738, disclose that the fertile period as well as time of ovulation can be predicted by monitoring the concentration of a volatile organic compound, or of urea, or both, in vaginal secretions. However, in this case, the fertile period was believed to be only four days out of the entire menstrual cycle. In one embodiment of this invention, urea is monitored, and a first increase in concentration occurs approximately 5 to 6 days prior to the time of ovulation. At least four days after the initial increase in urea concentration, a second urea increase is seen which occurs from 48 hours before to coincidental with the time of ovulation. None of the compounds monitored is disclosed to have any connection with levels of calcium or magnesium in saliva.

Preti et al., in U.S. Pat. No. 4,119,089, teach that the fertile period and time of ovulation can be predicted by assaying for volatile sulfur-containing constituents of mouth air, the levels of which are said to peak or spike approximately 5 to 7 days prior to ovulation and again at the time of ovulation. The volatile sulfur content of mouth air is thought to be responsive to elevated levels of female sex hormones. This assay relies upon aliquots of mouth air rather than on saliva.

Vietes, U.S. Pat. No. 3,813,222, discloses determining ovulation time and fertility in females by detecting the presence of small amounts of anterior pituitary hormone, estrogen, in urine, blood, serum or plasma. In this case the fertile period is believed to be immediately prior to ovulation.

Scherr, in U.S. Pat. No. 3,434,801, discloses diagnostic test material for determining ovulation based upon analyzing chloride ionic concentration of female body fluid, such as cervical, nasal and salivary mucus. This test is based upon levels of sodium chloride in the fluid.

However, there is a need for a simple yet reliable test that can predict the fertile period with accuracy, rather than merely the time of ovulation. This need was re-emphasized by Wilcox et al., op cit., who found that the last day of a woman's fertile period is the day of ovulation.

Saliva is readily available for sampling both by a physician and a patient. Therefore, a good salivary test will fit the criteria for simplicity. Many constituents of saliva have been studied and their relationship to the menstrual cycle and ovulation has been determined. These constituents include proteins, amino acids, urea, mucin, sugars, electrolytes, citric acid, and enzymes such as amylase and alkaline phosphatase. Most of these constituents bear no precise relationship to the fertile period of a female.

Goldman, in U.S. Pat. No. 4,358,288, observed that some unnamed component in saliva changed about 0–7 days prior to the ovulation date. Since it was assumed that the fertile period coincided with ovulation, this method did not absolutely detect the fertile period of a woman, but was merely a predictor of ovulation. The peak of the fertile period is assumed to occur at ovulation and to continue for seven to nine days afterward.

Regas et al., in U.S. Pat. No. 4,770,186, disclose that by measuring the electrical resistivity of saliva, the onset of ovulation can be determined six to two days prior to ovulation. Regas et al. determined that the major factor for the observation was probably due to the rapid change in salivary sodium ion concentration due to hormonal changes. In this case, the fertile period is believed to occur during the 72 hours prior to ovulation. This method works best when used in conjunction with monitoring vaginal electrical resistance. This method requires an instrument which includes measuring sensors and a display screen.

Other proposed methods for predicting ovulation range from a vaginal probe monitoring the redox biochemistry of the vaginal fluid (Conception Technology, Inc.) to checking the ferning pattern of dried saliva on a glass slide using a microscope (Rydberg, *Acta Obst. et Gyn. Scandinav.* 28:172, 1948).

Many studies of changes or electrolytes during the menstrual cycle had been reported. Brawley and Sedwick (1938) concluded that the use of salivary calcium as a diagnostic tool would have a rather limited utility, because of the wide range in standard values. Puskulian (1972) found a decrease in calcium concentration and sodium to potassium ratio using acid stimulated whole saliva at mid-cycle in eight women, while Tenovuo et al. (1981) and Ben-Aryeh et al. (1978) could not find the same variations in saliva during the menstrual cycle and concluded that monitoring electrolytes in whole saliva was not useful in estimating ovulation times. Ferguson (1982) was also unable to find any consistent variation in acid-stimulated whole parotid saliva electrolytes through the menstrual cycle in ten women. Measuring electrolytes in saliva samples for predicting the fertile period prior to ovulation therefore has remained unsuccessful.

SUMMARY OF THE INVENTION

It is an object of the present invention to provide a method for simply and reliably detecting the fertile period in a female.

It is another method to provide a method for detecting fertility using saliva as the body fluid analyzed.

The present inventors have unexpectedly found that when unstimulated saliva samples were collected with a well controlled protocol, the calcium and magnesium concentrations always exhibit a rapid drop (e.g., 0.8–1 nM over one day) one to five days prior to ovulation. This pattern can be monitored either by any calcium or magnesium sensitive test protocol, such as calcium and/or magnesium specific dyes or pigments, ion selective electrodes, or other means. The resulting threshold spot test, flow through test, strips, cards, charts, probes, meters, and the like, can be used as a simple means to predict the correct dates of the fertile period prior to ovulation.

The method includes using a reagent composition capable of interacting with saliva to produce a detectable and measurable response that can be directly correlated to the fertile period of a human female. For home use, the reagent composition preferably produces a visually detectable response. For laboratory use, the reagent composition produces a response that is detectable visually or by instrument. The method is suitable for (but not limited to) dry phase assays, wherein the reagent composition is incorporated into a carrier matrix of a detection device. The carrier matrix of the detection device may comprise bibulous porous materials such as filter paper, or such nonbibulous porous materials as a permeable strip, layer or membrane of a polymeric material. Preferably, a reagent composition to detect calcium and/or magnesium, or total ionic concentration, is homogeneously incorporated into the carrier matrix, and the carrier matrix then holds the reagent composition homogeneously throughout the carrier matrix in a known concentration, while maintaining the permeability of the carrier matrix to saliva.

Alternatively, semi-quantitative or quantitative tests can be used for detecting calcium and magnesium ion concentrations.

DETAILED DESCRIPTION OF THE INVENTION

Samples

Figure 1:
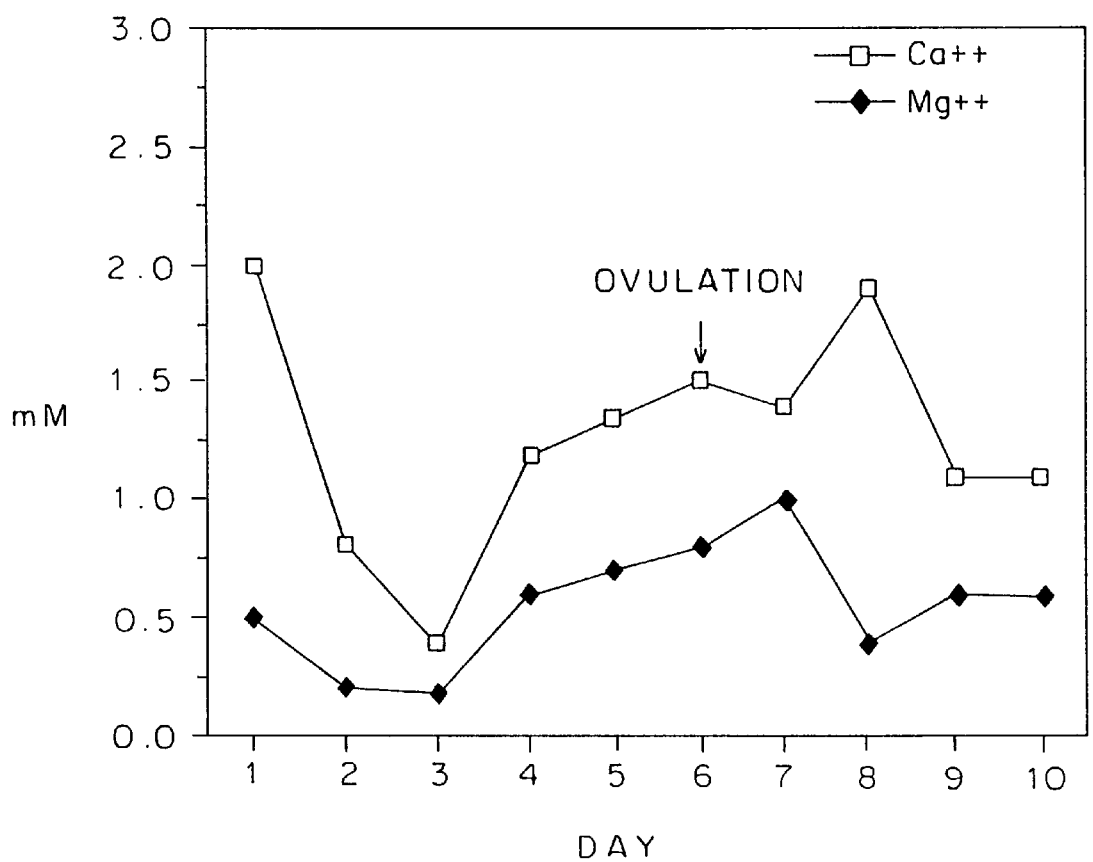
FIG. 1 shows the calcium and magnesium concentration in saliva in the days before and after ovulation.

Although the present invention is primarily intended for use by human females, it is also equally applicable to other female mammals, and in particular to domestic cattle, horses, pigs, goats, sheep, llamas, cats, dogs, rabbits, hamsters, mice and rats. For nonhuman animals, it is necessary to first establish the correlation between calcium and magnesium levels and the fertile period to serve as a reference. In breeding these animals, it is of primary importance to determine the fertile period of a given female animal so that access to a male need be provided for the shortest length of time. This is particularly true where stud service fees are involved and where detection of the fertile period of the female animal allows for the more efficient utilization of each stud animal.

The test of the present invention is performed on a saliva sample. The sample is preferably whole saliva, however, it may be found to be helpful to isolate and test one or more saliva components, such as submandibular or parotid saliva, separately. Samples are preferably taken at least once daily, however, samples may be taken more or less frequently if the desired level of accuracy in predicting the fertile period is still attained.

Sample Testing

The testing of the sample may be qualitative, semi-quantitative, or quantitative, and may be for calcium concentration and/or magnesium concentration.

The calcium and magnesium can be analyzed in saliva using any conventional test for calcium and/or magnesium. Examples of such tests are given in the following U.S. patents, the entire contents of which are hereby incorporated by reference:

| | |
|---|---|
| Sulkowitch | 2,824,824 |
| Jordan | 3,006,735 |
| Fraguada et al. | 3,457,045 |
| Gindler | 3,754,865 |
| Helger | 3,798,000 |
| Rathje | 3,854,880 |
| Cleaver | 3,934,977 |
| Stavropoulos et. al. | 3,938,954 |
| Simpson et al. | 4,293,307 |
| Mezei et al., | 4,382,122 |
| Denney et al. | 4,383,043 |
| Sarig et al. | 4,399,003 |
| Luderer | 4,425,427 |
| Denney | 4,454,230 |
| Yamazato | 4,503,156 |
| Springer, Jr. et al. | 4,532,217 |
| Arai | 4,594,225 |
| Premoli et al., | 4,618,587 |
| Young et al. | 4,724,216 |
| Smith-Lewis et al. | 4,753,890 |
| Toner et al. | 4,795,712 |
| Gibbons | 4,820,647 |
| Musacchio et al. | 4,870,024 |
| Wahl et al. | 4,871,678 |
| Tanaka et al. | 4,871,679 |
| O'Brien et al. | 4,904,605 |
| Tanaka et al. | 4,966,784 |
| Porter et al. | 4,992,382 |
| Lau et al. | 5,055,407 |
| Denney | 5,057,435 |
| Miller, Jr. et al. | 5,077,221 |
| Sunahara et al. | 5,108,905 |
| Quinn et al. | 5,192,691 |
| Artiss et al. | 5,215,922 |
| Babb et al. | 5,215,925 |
| Chapoteau et al. | 5,262,330 |
| Charlton | 5,300,439 |
| Bloczynski et al. | 5,310,888 |
| Zimmerle | 5,350,694 |
| Steinman | 5,397,710 |
| Lakowicz et al. | 5,409,835 |
| Shu et al. | 5,424,214 |
| Altura et al. | 5,460,972 |
| Denton et al. | 5,482,866 |
| Vo-Dinh et al. | 5,496,522 |
| Katerinopoulos et al. | 5,501,980 |

Home testing is preferably performed by qualitative methods with a visual readout. In essence, the device takes the form of a matrix associated with at least calcium or magnesium sensitive dye or pigments which undergoes a visible change in the presence of a clinically significant threshhold concentration of the ion. Suitable calcium sensitive dyes and pigments include Calmagite, phthalein blue, phthalein purple, Calcon carboxylate acid, hydroxy naphthol blue, Arsenazo I. Suitable magnesium sensitive dyes and pigments include Calmagite. The threshhold concentration may be adjusted by means of any suitable chemical or physical agent, such as calcium or magnesium ion chelating agent, e. g. EDTA (N, N, N',N'-Ethylenediaminetetraacetic acid). (A threshhold adjusting agent is not necessary for a qualitative assay.) The matrix may be any material capable of retaining and presenting the dye or pigment for the desired shelf and use life, and which does not substantially interfere with the assay. Suitable matrix materials include conventionally used materials such as filter paper, cellulose, etc. The dye or pigment may be associated with the matrix by any physical or chemical means, including, e.g. impregnation, coating, and covalent attachment. The matrix may take any convenient physical form, such as a card, pad, strip or dipstick.

The concentration of calcium and/or magnesium in saliva can be monitored very simply and reliably using a dip stick or a card method, such as for monitoring water hardness. In the simplest format, reagent pads can be formulated as follows. A preferred reagent pad is described below:

Formulation #1

Dye: Erichromblack T (3-hydroxy-4-[(1-hydroxy-2-naphthalenyl)azo]-7-nitro-1-naphthalenesulfonic acid monosodium salt)

Buffer: pH 9–10

Matrix: Whatman filter paper

Threshold adjustment: EDTA (N, N, N', N'-ethylene diamine tetraacetic acid)

Formulation #2

Dye: Thymolphthalein complexone

Buffer: CAPS (3-[Cyclohexylamino]-1-propanesulfonic acid)

buffer, pH=10–11

Matrix: Watman filter paper

Threshold adjustment: EDTA

The reagents were impregnated onto the filter paper and dried. A threshold test pad was made with a total hardness threshold set at 0.5 mM, and the test strip contained one single pad. Whole saliva was obtained by a sponge swab, and then applied to the pad by saturation. The pad turns pink until the cycle reaches 1 to 5 days before ovulation; at that time, the calcium level in the saliva has dropped, and the color of the pad remains blue.

An alternate to the reagent pad described above is a test strip containing multiple pads or stripes. Each pad represents a higher threshold for total calcium and magnesium concentrations. Saliva samples were introduced onto these pads on the test strip and a semi-quantitative reading was obtained for each day of the cycle. At 1 to 5 days prior to ovulation, a drastic dip in the total hardness of saliva was observed.

Other methods to monitor the changes in calcium and magnesium levels can also be used. Ion selective electrodes for calcium and magnesium are commonly available and can be used to monitor changes in calcium and magnesium concentrations in saliva. A small hand held reflectometer with test strip built to give different color shades according to concentrations of calcium and magnesium can also be used for monitoring. Gravimetric methods, flame spectroscopy, atomic absorption spectroscopy and other methods know to the art are also useful in performing the testing.

Any conventional quantitative method can be used for detecting calcium and magnesium in saliva. An example of such a method uses a quantitative calorimetric calcium reagent kit using o-cresolphthalein complexone from Sigma Diagnostics, St. Louis, Mo. and a quantitative calorimetric magnesium reagent kit, also from Sigma Diagnostics. To assay for calcium and magnesium using these kits, saliva samples were assayed in a HO8451A UV-Vis spectrophotometer following the manual procedures outlined by Sigma Diagnostics. Calcium and magnesium concentrations were reported in mM units.

Alternatively, the calcium and magnesium concentrations in saliva can be assayed based upon the specific gravity of the saliva; as the calcium and magnesium concentrations increase, the specific gravity of the saliva increases as well. The specific gravity can be measured using a carrier matrix which includes a reagent composition capable of interacting with an aqueous test sample to provide a visually or instrumentally detectable and measurable response that correlates to the specific gravity of the aqueous sample. An example of such a reagent comprises a molybdate-dye complex indicator such as a molybdatepyrocatechol violet complex, a protein, a chelating agent, and a suitable buffer. This type of test is described more completely in Lau et al., U.S. Pat. No. 5,055,407, the entire contents of which are hereby incorporated by reference.

In one embodiment, the dip and/or trugh in the calcium and/or magnesium ion concentration is automatically discerned by electronic analysis of successive readings, and a positive signal displayed.

Experimental Example

Fifty women ranging in age from 24 to 45 were recruited for the clinical study. Basal temperature readings were taken as soon as the eyes were opened in the morning, and unstimulated whole saliva samples were collected by spitting into sample cups. The sample cups were then immediately placed into a freezer pending analysis. Conductance and pH measurements were made for each sample, and the concentrations of calcium and magnesium were measured by either calorimetric assays or ion selective electrodes. A typical variation pattern of calcium and magnesium around the time of ovulation is shown in FIG. 1. It was noted that the level of calcium and magnesium ions took a drastic dive in whole saliva concentrations (the predive value value being two- to five-fold the postdive value) at a period from one to five, especially, three to four days prior to ovulation. The drastic decrease in calcium and magnesium concentrations was conveniently monitored by calorimetric assays, or even commercially available water hardness test strips. The accompanying changes in pH and conductance were also monitored during these periods and are shown in FIG. 2.

Figure 2:
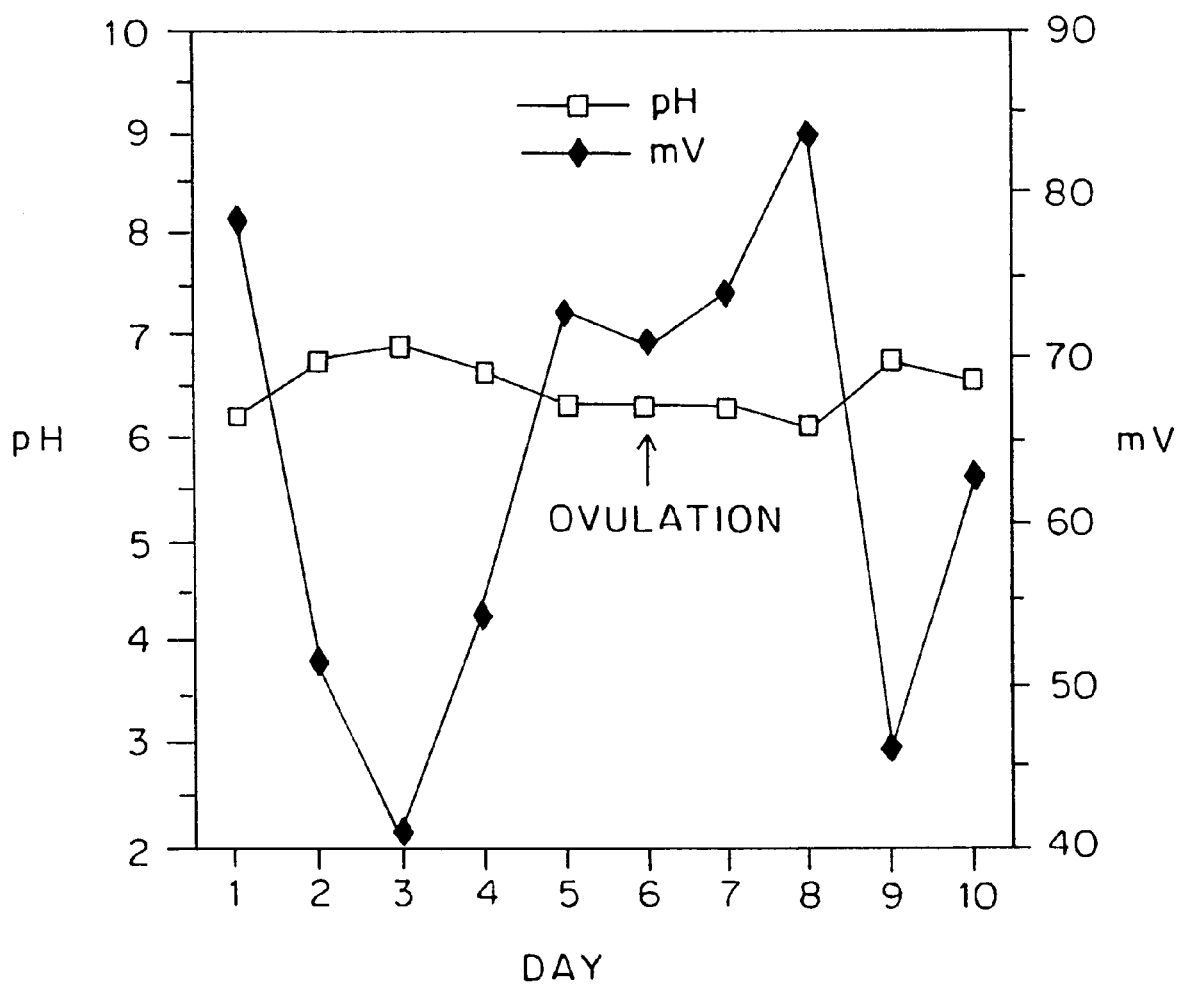
FIG. 2 shows the pH of saliva samples taken over the same time period as in FIG. 1, which only slight variation in pH over the period, and no significant change in pH at the period immediately prior to ovulation. By comparison of FIGS. 1 and 2, it is apparent that changes in calcium and magnesium concentration, and in conductance, are simultaneous.
Figure 3:
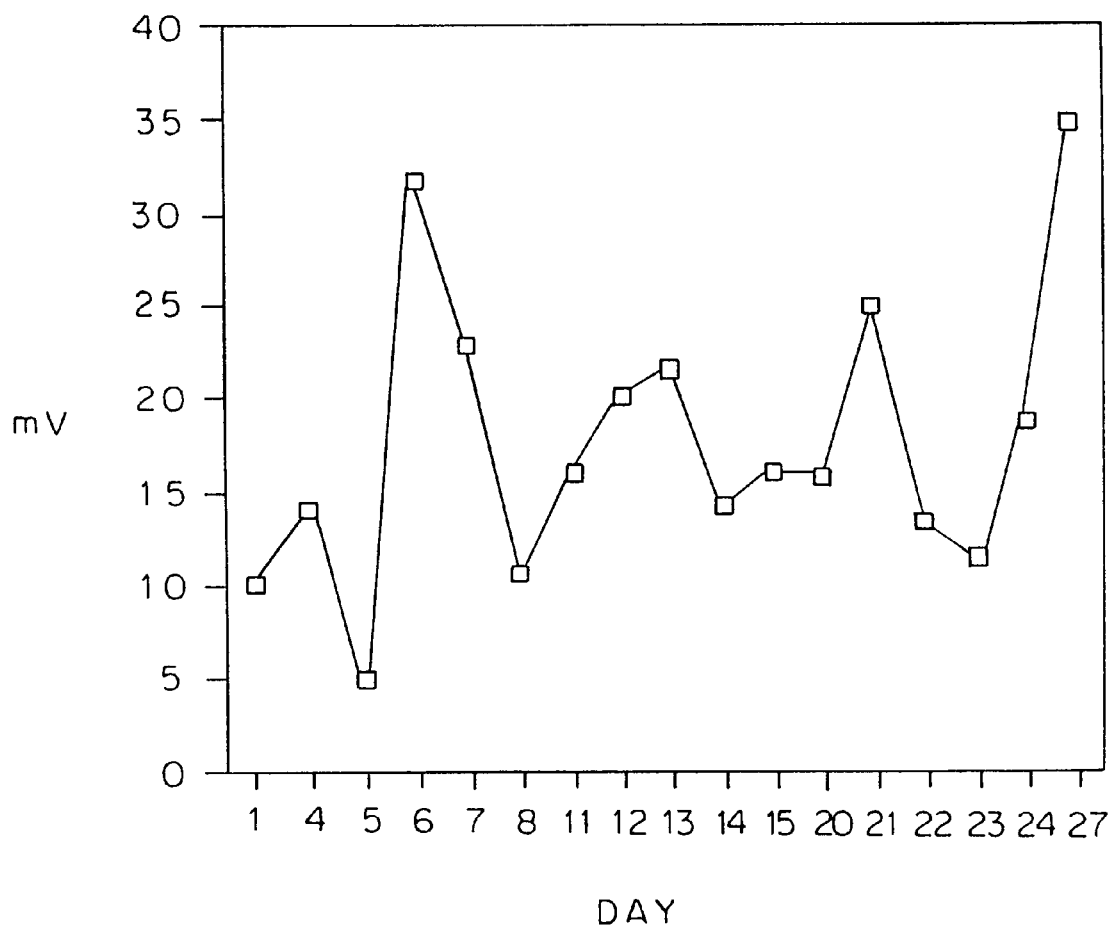
FIG. 3 shows the conductivity of saliva samples taken over a period of 26 days without following the sampling protocol.

It can readily be seen from FIGS. 1 and 2 that there is no observable relationship between pH and the calcium and magnesium ion concentration changes. However, the conductance change tracks the calcium and magnesium ion change time frame exactly. Saliva samples collected without following the protocol described did not show the same pattern of ionic changes, as shown in FIG. 3. It therefore is desirable to collect the salival sample in the morning before breakfast, or any activity.

All of the patents and articles cited herein are hereby incorporated in their entirety by reference.

Test Interpretation

In a qualitative assay, the assay determines whether the calcium or magnesium level exceeds a threshhold concentration.

In a quantitative assay, the assay determines the calcium or magnesium level, and this level is correlated with data for a comparable patient population.

Correlation with Other Tests

The tests of the present invention may be used, simultaneously or sequentially, in conjunction with other tests for fertility and/or ovulation, such as the tests set forth in the BACKGROUND, so as to provide still greater confidence in the determinations made.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. The means and materials for carrying out various disclosed functions may take a variety of alternative forms without departing from the invention. It is to be understood that the phraseology or terminology employed herein is for the purpose of description and not of limitation.

What is claimed is:

1. A method for predicting the fertile period in a female comprising monitoring unstimulated saliva collected immediately upon arising in the morning for a decline in the concentrations of calcium, magnesium, or both, sufficient to indicate that ovulation will occur in one to six days.

2. The method according to claim 1 wherein the monitoring is conducted with a dip stick or test strip.

3. The method according to claim 1 wherein Erichrome Black T is used as an indicator for calcium and magnesium.

4. The method according to claim 1 wherein thymolphthalein complexone is used as an indicator for calcium and magnesium.

5. The method according to claim 1 wherein the changes are monitored quantitatively.

6. The method of claim 1 wherein calcium concentrations are monitored.

7. The method of claim 1 wherein magnesium concentrations are monitored.

8. The method of claim 1 wherein the calcium or magnesium concentrations are recorded with a device which produces a detectable signal upon detecting a decline in calcium or magnesium concentration sufficient to be indicative that ovulation will occur in one to six days.

* * * * *